United States Patent
Komiyama

(10) Patent No.: US 6,533,579 B2
(45) Date of Patent: Mar. 18, 2003

(54) INTRAORAL DIFFUSION TYPE ADMINISTRATION DEVICE INCORPORATED IN REMOVABLE DENTAL RESTORATION

(76) Inventor: Tomonobu Komiyama, 2032-2 Daitakubo, Saitama-shi, Saitama (JP)

( * ) Notice: Subject to any disclaimer, the term of this patent is extended or adjusted under 35 U.S.C. 154(b) by 0 days.

(21) Appl. No.: 09/805,496

(22) Filed: Mar. 13, 2001

(65) Prior Publication Data

US 2001/0038994 A1 Nov. 8, 2001

(30) Foreign Application Priority Data

Mar. 16, 2000 (JP) .................................... 2000-074704

(51) Int. Cl.[7] .............................................. A61C 17/00
(52) U.S. Cl. ........................................ 433/80; 604/17
(58) Field of Search ...................... 433/80, 229; 604/77

(56) References Cited

U.S. PATENT DOCUMENTS

| | | | |
|---|---|---|---|
| 2,470,679 A | | 5/1949 | Beers |
| 3,600,807 A | * | 8/1971 | Sipos .......................... 433/167 |
| 3,878,610 A | | 4/1975 | Coscina |
| 3,978,585 A | | 9/1976 | Holcomb |
| 4,106,501 A | * | 8/1978 | Ozbey et al. .................. 433/80 |
| 4,227,877 A | | 10/1980 | Tureaude et al. |
| 4,676,752 A | * | 6/1987 | Lefkowitz .................... 433/229 |
| 5,090,903 A | * | 2/1992 | Taylor et al. ................ 433/229 |
| 5,190,457 A | | 3/1993 | Schreinemakers |
| 5,842,860 A | * | 12/1998 | Funt ........................... 433/229 |
| 6,206,692 B1 | | 3/2001 | Komiyama |

* cited by examiner

*Primary Examiner*—Cary E. O'Connor
(74) *Attorney, Agent, or Firm*—Allen, Dyer, Doppelt, Milbrath & Gilchrist, P.A.

(57) ABSTRACT

A dental device includes a removable dental restoration device having at least one sector positionable adjacent an opening of a salivary gland of a human wearer. At least one chamber is provided for storing a material for administration. The chamber has a permeable wall disposed near the sector. The dental device has a tube having one end connected in fluid communication with the chamber and an opening therethrough at a predetermined position in spaced relation from the one end. Shutters are provided to effect a shutting and an opening of the permeable wall and the tube opening. The permeability of the wall permits saliva to enter the chambers to dissolve the administration material, and the concentration gradient in the tube results in a gradual diffusion of the solution into the mouth.

7 Claims, 5 Drawing Sheets

100
INTRAORAL DIFFUSION TYPE ADMINISTRATION DEVICE INCORPORATED IN REMOVABLE DENTAL RESTORATION

BACKGROUND OF THE INVENTION

The present invention relates to an intraoral diffusion type administration device incorporated in a dental restoration, particularly to a device incorporated in a dental restoration, such as a complete denture, a partial plate denture, and a mouthpiece, for gradually diffusing and administering a deodorant or aromatic for eliminating bad breath, a general drug, and/or a nutrient in a mouth. Moreover, the present invention relates to a dental restoration in which such device is incorporated.

Brushing, removal treatment of dental plaque or calculus, operation for periodontal disease or the like is usually carried out for prevention of bad breath or for mouth cleaning. A gargling agent is also possibly used for these purposes.

Most kinds of drugs and nutrients for medical care or health care are usually administered orally in the form of tablet or powder.

If the brushing, removal treatment of dental plaque or calculus, operation for periodontal disease or the like are carried out, clean state in a mouth will be kept providing no bad breath for the time being. However, the clean state in a mouth will not last long to cause bad breath again. Even if a gargling agent is used, its effect cannot be maintained for a long time.

Moreover, when a patient, in particular, an old person or a child take a drug or nutrient, he or she often feels hardness in the case of tablet, or coughs in the case of powder. Sometimes, the patient cries with aversion refusing it strongly from the first.

Furthermore, in many cases, the intake of a nutrient, a sweetener or the like tends to be excessive, which frequently leads to an adverse reaction.

SUMMARY OF THE INVENTION

It is an object of the present invention to provide a device incorporated in a dental restoration for diffusing and administering a deodorant or aromatic for eliminating bad breath, a general drug, a sweetener or the like continuously, stably and smoothly without hardness and aversion, and to provide a dental restoration in which such device is incorporated.

In order to achieve the object, an intraoral diffusion type administration device incorporated in a removable dental restoration comprising: chambers disposed near openings of saliva glands in a human mouth for storing an administration material; permeable walls provided at said chambers; tubes having one ends connected to said chambers and having openings at predetermined positions; and shuttering means, provided at said walls and at said openings of said tubes, for shutting and opening them is provided according to the present invention.

Preferably, the walls are made of porous thin-film type semipermeable membrane. The walls should be physically strong and chemically stable, and harmless to tissues and organs in a mouth. Moreover, of course the administered material should be harmless to a human body.

It is preferable to dispose shuttering means (door, window, shutter, valve and the like) which can open when in use (not in eating and drinking) and close when not in use (in eating and drinking), resulting in the effective administration without loss. Removable shuttering means also may be used.

If a deodorant for eliminating bad breath is used as the administration material in the present invention, the effect can last long stably. Moreover, if an aromatic for "fresh" mouth is used in the present invention as the administration material, the effect can last long stably.

If a general drug in solid state (tablet or powder) is used for medical care as the administration material in the present invention, the drug is dissolved and diffused into a mouth, so that even an old person or child can take it naturally and smoothly without feeling hardness and coughing.

If a nutrient or a sweetener for health care is used as the administration material in the present invention, the intake thereof having a tendency to be excessive may be suppressed to a certain optimum amount.

The chamber is previously charged with the administration material in the form of solid, such as tablet and powder, or in the form of solution. Moreover, a colloidal material or a surface active agent may be used as the administration material. Furthermore, a cleaning agent for a dental restoration itself including the device of the present invention may be used as the administration material.

It is preferable that the positions of the permeable walls in a dental restoration are in the neighborhood of an opening of a saliva gland, because there is plenty of saliva permeable into the chamber.

The tubes may have some branches so that the administration material previously stored in the chamber could be dissolved in saliva permeable through the walls and that the resultant solution could be distributed and diffused widely in a mouth. Moreover, the tubes may have a plurality of openings at predetermined positions.

The dental restoration includes an apparatus for occlusal treatment, a mouth guard and a mouthpiece for sports or protection, as well as a complete denture and a partial plate denture.

The term "administration" used in this specification should not be restricted to the meaning that the administration material is sent through a mouth and is ingested by digestive organs. It also includes the meaning that the administration material (for example deodorant) acts in a mouth. Moreover, "permeability" generally means the action of a semipermeable membrane which is permeable by small particles and not by large ones, thus in the specification it means the action of being permeable by saliva but not permeable by the administration material.

In an intraoral diffusion type administration device according to the present invention, the chamber is previously charged with the administration material. Saliva in a mouth permeates the chamber through the walls by permeability of the walls, so that the administration material is wetted, dissolved and stored. The solution in the tube connected to the chamber has higher concentration near the chamber and lower concentration near the opening of the tube. The concentration gradient permits the solution of the administration material to be diffused from the opening of the tube into the mouth.

BRIEF DESCRIPTION OF THE DRAWINGS

Preferred embodiments of the invention are described by way of example with reference to the accompanying drawings in which.

DETAILED DESCRIPTION OF THE PREFERRED EMBODIMENTS

The embodiments of the present invention are described below with reference to the drawings.

Figure 1:
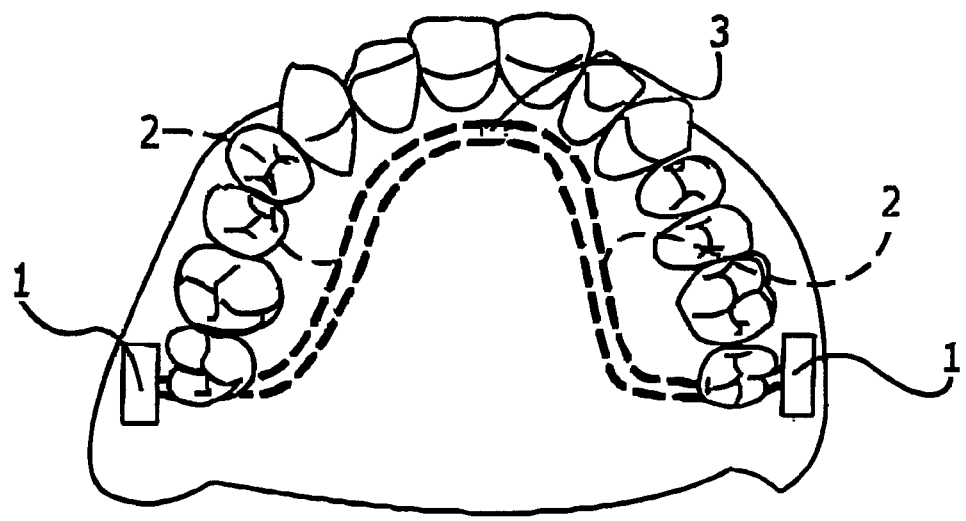
FIG. 1 is a plan view of a maxillary complete denture in which an intraoral diffusion type administration device of the present invention is incorporated.
Figure 2:
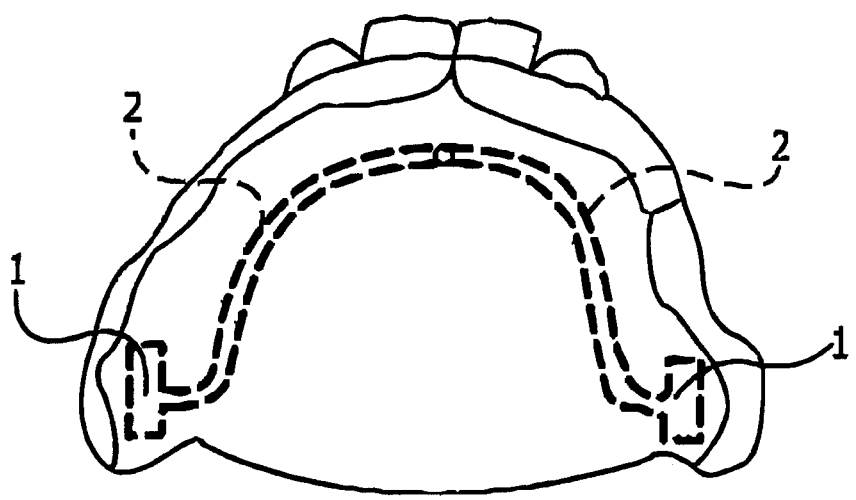
FIG. 2 is a bottom view of the maxillary complete denture shown in FIG. 1.

FIGS. 1 and 2 are a plan view and a bottom view, respectively, of a maxillary complete denture in which an intraoral diffusion type administration device of the present invention is incorporated. In these figures, numeral reference 1 indicates a chamber for storing a solution of a previously encapsulated administration material in saliva permeating the chamber. Numeral reference 2 indicates a tube for sending the solution of the administration material stored in the chamber 1 to an opening 3 to diffuse it into a mouth. The chamber 1 is provided with a wall, or semipermeable membrane having permeability. The tube 2 is embedded into a plate of the complete denture. Although in the figures the chamber 1 is disposed on the plate of the complete denture, only the wall part of the chamber 1 may be exposed outward and other parts may be embedded into the plate. The opening 3 is open to the mouth.

The reason the chamber 1 is positioned as shown in FIGS. 1 and 2 is that this position (near a maxillary tuberosity) is in the neighborhood of an opening of a parotid gland so that the chamber 1 can be in contact with plenty of saliva.

Figure 5:
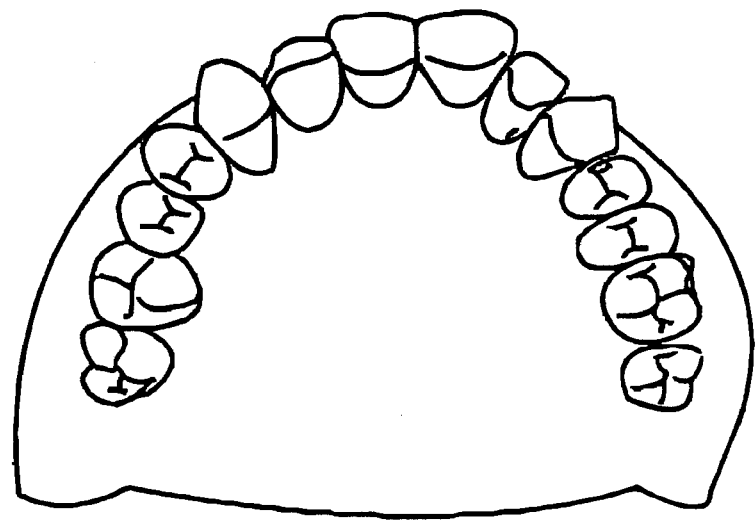
FIG. 5 is a plan view of a maxillary complete denture without an intraoral diffusion type administration device of the present invention.
Figure 6:
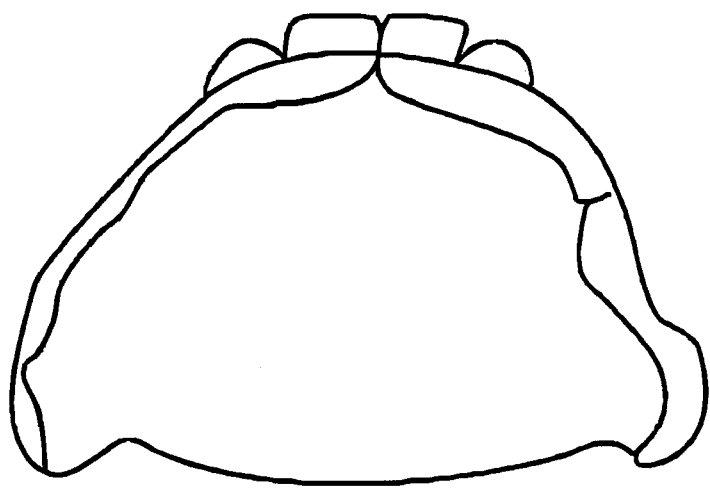
FIG. 6 is a bottom view of the maxillary complete denture shown in FIG. 5.

For reference FIGS. 5 and 6 show a plan view and a bottom view, respectively, of a maxillary complete denture without an intraoral diffusion type administration device of the present invention.

Figure 3:
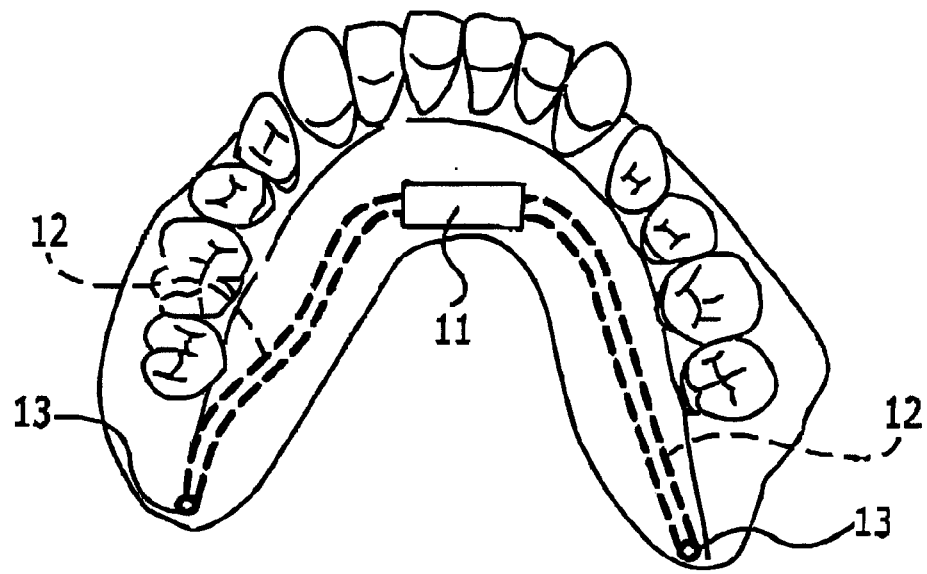
FIG. 3 is a plan view of a mandibular complete denture in which an intraoral diffusion type administration device of the present invention is incorporated.
Figure 4:
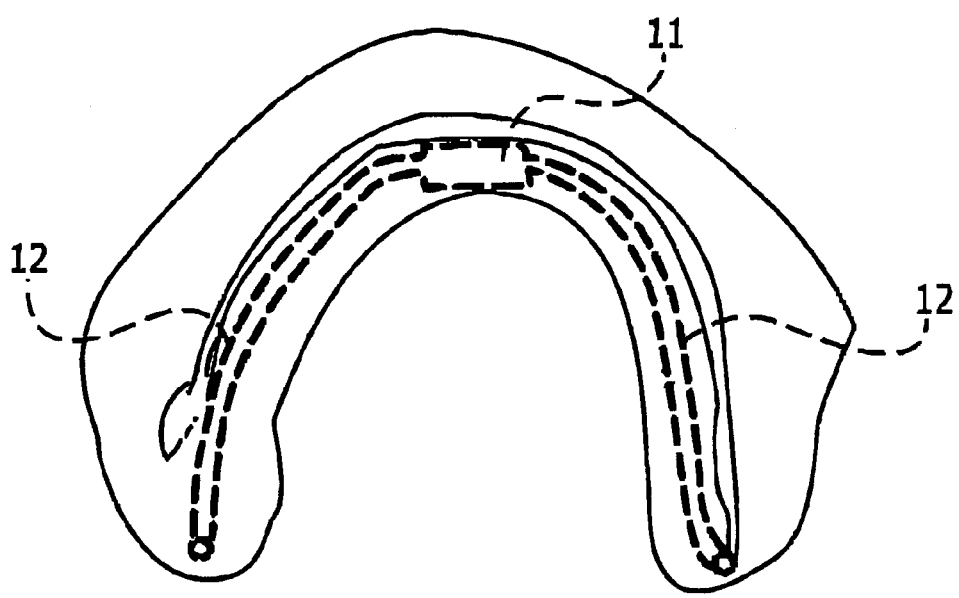
FIG. 4 is a bottom view of the mandibular complete denture shown in FIG. 3.

FIGS. 3 and 4 are a plan view and a bottom view, respectively, of a mandibular complete denture in which an intraoral diffusion type administration device of the present invention is incorporated. In these figures, numeral reference 11 indicates a chamber for storing a solution of a previously encapsulated administration material in saliva permeating the chamber. Numeral reference 12 indicates a tube for sending the solution of the administration material stored in the chamber 11 to an opening 13 of the tube to diffuse it into a mouth. The chamber 11 is provided with a wall, or semipermeable membrane having permeability. The tube 12 is embedded into a plate of the complete denture. Although in the figures the chamber 11 is disposed on the plate of the complete denture, only the wall part of the chamber 11 may be exposed outward and other parts may be embedded into the plate. The opening 13 is open to the mouth.

The reason the chamber 11 is positioned as shown in FIGS. 3 and 4 is that this position (near a sublingual caruncule) is in the neighborhood of openings of a submandibular gland and a sublingual gland so that the chamber 11 can be in contact with plenty of saliva.

Figure 7:
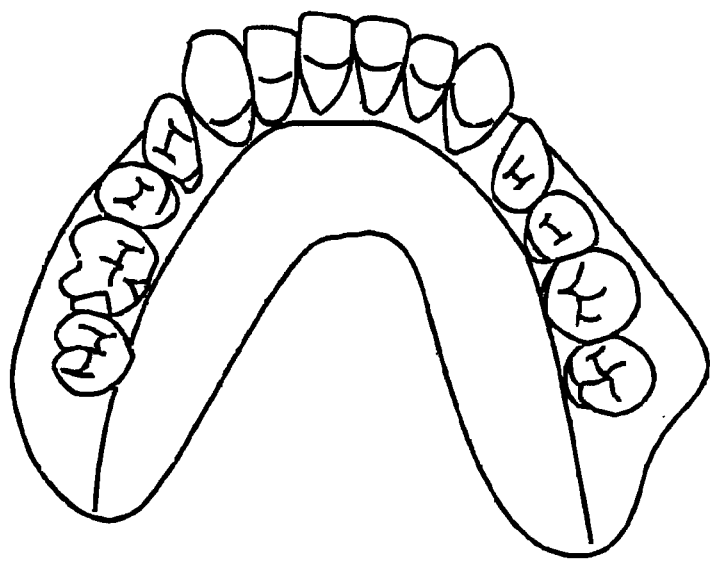
FIG. 7 is a plan view of a mandibular complete denture without an intraoral diffusion type administration device of the present invention.
Figure 8:
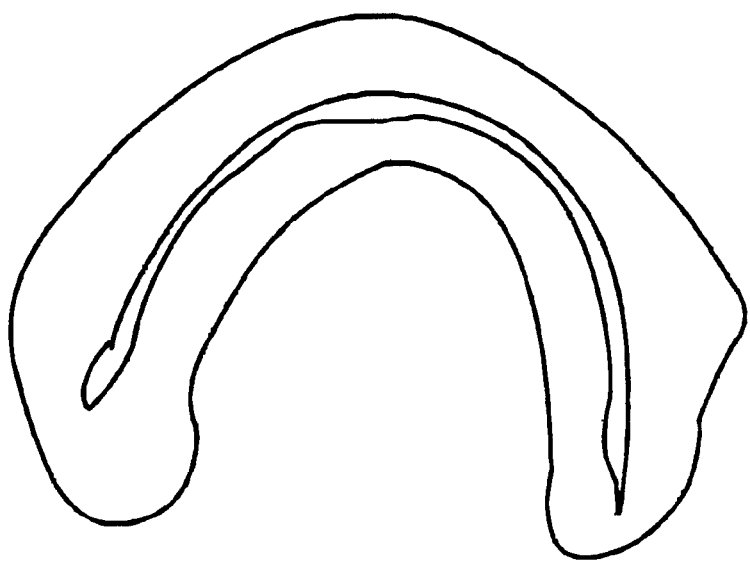
FIG. 8 is a bottom view of the mandibular complete denture shown in FIG. 7.

For reference FIGS. 7 and 8 show a plan view and a bottom view, respectively, of a mandibular complete denture without an intraoral diffusion type administration device of the present invention.

Figure 9:
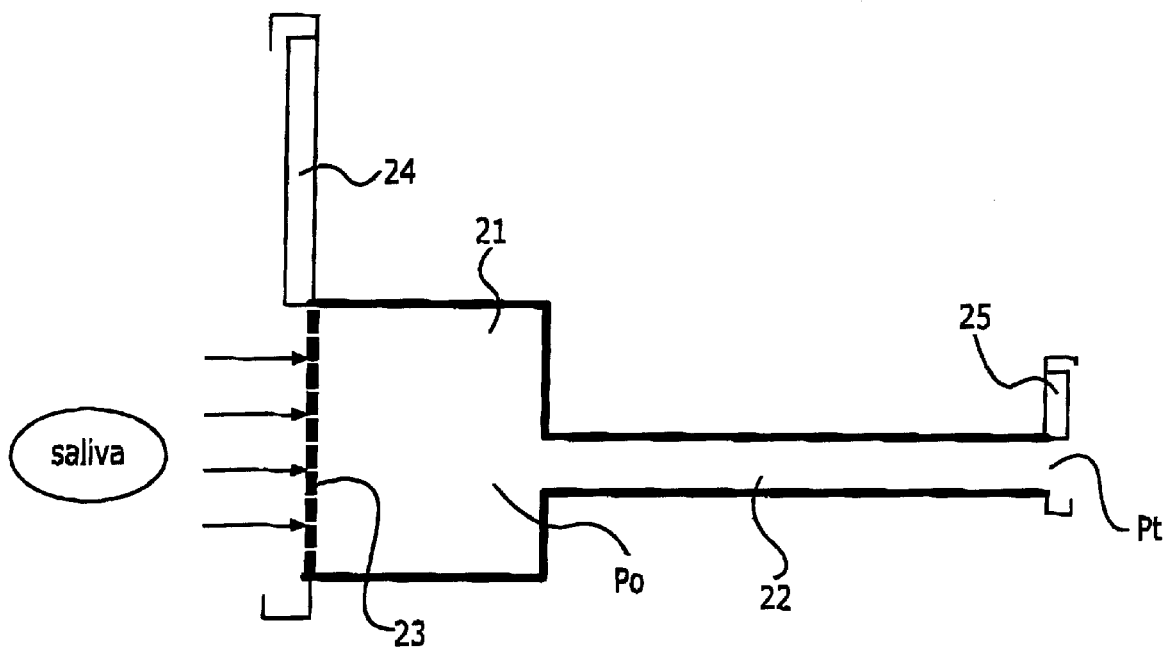
FIG. 9 is a diagrammatic illustration of an intraoral diffusion type administration device of the present invention.

Referring now to FIG. 9, the action of the embodiments of the present invention is illustrated.

FIG. 9 is a diagrammatic illustration of an intraoral diffusion type administration device of the present invention. A chamber 21 is previously charged with the administration material such as a deodorant, an aromatic, a general drug, a nutrient or the like in the form of powder, solid or solution. A wall 23 is a semipermeable membrane, which is permeable by saliva but not by the administration material. Namely, the wall 23 has permeability, permitting the permeation of saliva into the chamber 21 keeping the administration material within the chamber 21. The permeating saliva gives osmotic pressure to the semipermeable membrane. If shuttering means 24,25 of the administration device is open, saliva enters the chamber 21 through the wall 23 to wet and dissolve the administration material. As a result, the solution in a tube 22 has a higher concentration $C_i$ at a position Po nearer the chamber, and a lower concentration $C_t$ at a position Pt nearer the opening, which generates concentration gradient, so that the solution of the administration material is transported and diffused into a mouth. As described above, according to the present invention, the permeability of the wall 23 and the concentration gradient in the tube 22 permit the gradual diffusion of the solution of the administration material into a mouth.

The time required for administration, the dose of the administration material, and the administration rate may be adjustable by properly determining or designing the amount and form of the administration material previously stored, the dimension and permeability of the wall, the diameter and length of the tube and the like.

The following advantages are obtained by the present invention.

(i) In the case that a deodorant or an aromatic is used as the administration material, it can be diffused into a mouth continuously, stably and naturally, so that clean and comfortable state in a mouth can be kept for a long time without bad breath. Thus, the present invention is effectively applicable to the field of spices, cosmetics and the like and to the study and research of dental restorations, orthodontics, periodontal health, mouth health and the like.

(ii) In the case that a general drug or a nutrient is used as the administration material, it can be diffused gradually and naturally into a mouth, so that a patient or user can swallow it easily without feeling hardness or coughing. Thus, the present invention is effectively applicable to the intraoral diffusion type administration of a drug prescribed by a doctor, a dentist, or a pharmacist, and of a nutrient for health care, cosmetology, sports and the like. Further, it is also useful to the study and research in general pharmacy.

What is claimed is:

1. A dental device comprising:

a removable dental restoration device having at least one sector positionable adjacent an opening of a salivary gland of a human wearer;

at least one chamber for storing a material for administration, the chamber having a permeable wall disposed near the sector;

a tube having one end connected in fluid communication with the chamber and having an opening therethrough at a predetermined position in spaced relation from the one end; and means for shuttering the permeable wall and the tube opening to effect a shutting and an opening thereof.

2. The device according to claim 1, wherein the chamber is adapted to store an administration material in a solution.

3. The device recited in claim 1, wherein the shuttering means open when in use and close when not in use.

4. The device recited in claim 1, wherein the administration material is selected from a group consisting of at least one of a deodorant for eliminating bad breath, an aromatic for eliminating bad breath, a general drug, nutrient, a colloidal materia, a cleaning agent for the dental restoration and the administration device.

5. A method for providing a material for delivery to a human comprising the steps of:

providing a dental device comprising:

a removable dental restoration device having at least one sector positionable adjacent an opening of a salivary gland of a human wearer;

at least one chamber for storing a material for administration, the chamber having a permeable wall disposed near the sector;

a tube having one end connected in fluid communication with the chamber and having an opening therethrough at a predetermined position in spaced relation from the one end; and means for shuttering the permeable wall and the tube opening to effect a shutting and an opening thereof; and introducing a material desired for administration to the human into the chamber.

6. The method recited in claim 5, further comprising the step of opening the shuttering means and placing the device into the mouth of the human.

7. The method recited in claim 5, wherein the administration material is selected from a group consisting of at least one of a deodorant for eliminating bad breath, an aromatic for eliminating bad breath, a general drug, nutrient, a colloidal materia, a cleaning agent for the dental restoration and the administration device.

* * * * *